United States Patent
Dijkman et al.

(10) Patent No.: US 9,138,256 B2
(45) Date of Patent: Sep. 22, 2015

(54) SURGICAL INSTRUMENT

(75) Inventors: Coen Dirk-Jan Dijkman, Weesp (NL); Johannes Franciscus Marinus Remmerswaal, Delft (NL); Sebastiaan Veersema, Utrecht (NL)

(73) Assignee: BASIQ B.V., Delft (NL)

( * ) Notice: Subject to any disclaimer, the term of this patent is extended or adjusted under 35 U.S.C. 154(b) by 746 days.

(21) Appl. No.: 13/496,955

(22) PCT Filed: Sep. 21, 2009

(86) PCT No.: PCT/NL2009/050566
§ 371 (c)(1),
(2), (4) Date: May 18, 2012

(87) PCT Pub. No.: WO2010/033030
PCT Pub. Date: Mar. 25, 2010

(65) Prior Publication Data
US 2012/0239056 A1 Sep. 20, 2012

(30) Foreign Application Priority Data

Sep. 19, 2008 (NL) .................................... 2002000

(51) Int. Cl.
*A61B 17/42* (2006.01)
*A61B 17/32* (2006.01)

(52) U.S. Cl.
CPC ................ *A61B 17/42* (2013.01); *A61B 17/32* (2013.01); *A61B 2017/320052* (2013.01)

(58) Field of Classification Search
CPC ............... A61B 17/0467; A61B 2017/320064; A61B 17/3201; A61B 10/02; A61B 17/30; A61B 2017/301; A61B 2017/303

USPC .......... 606/119, 210–211, 131; 600/185, 190, 600/197, 234

See application file for complete search history.

(56) References Cited

U.S. PATENT DOCUMENTS

| 2,329,264 A | 9/1943 | Glasser |
| 3,631,858 A * | 1/1972 | Ersek .......................... 606/120 |

(Continued)

FOREIGN PATENT DOCUMENTS

| EP | 1 645 238 A1 | 4/2006 |
| FR | 1 024 981 A | 4/1953 |
| WO | 00/57798 A1 | 10/2000 |

OTHER PUBLICATIONS

International Search Report, dated Nov. 19, 2009, from corresponding PCT application.

*Primary Examiner* — Ashley Fishback
*Assistant Examiner* — Sidharth Kapoor
(74) *Attorney, Agent, or Firm* — Gilberto M. Villacorta; Sunit Talapatra; Foley & Lardner LLP

(57) ABSTRACT

Surgical instrument and method for the removal of tension in a continuous portion of tissue. In order to prevent the further tear of tissue under tension when making an initial incision, it is proposed that the initial incision is made not at the edge of the tissue portion but at a point further along the tissue portion, preferably at the end point of the intended separation. From that point, the separation is made towards the edge of the tissue portion. The initial separation can be performed by way of incision, perforation and the like. To this end, a surgical instrument is proposed that, for example, can be provided with a cutting blade that is inclined at an angle in such a manner that when the blade is moved towards the opposing support member between which the tissue is held, the tissue is cut from the free end of the blade.

18 Claims, 4 Drawing Sheets

(56) References Cited

U.S. PATENT DOCUMENTS

| | | |
|---|---|---|
| 3,877,145 A | 4/1975 | Andrews |
| 4,938,215 A * | 7/1990 | Schulman et al. ............ 606/120 |
| 5,046,252 A * | 9/1991 | Ayuta et al. ..................... 30/258 |
| 5,312,420 A * | 5/1994 | Toso et al. ..................... 606/138 |
| 5,922,002 A * | 7/1999 | Yoon ............................. 606/170 |
| 5,984,939 A * | 11/1999 | Yoon ............................. 606/170 |
| 6,348,057 B1 * | 2/2002 | Porat ............................. 606/120 |
| 6,852,117 B2 * | 2/2005 | Orlowski ....................... 606/120 |
| 6,910,401 B2 * | 6/2005 | Tapper ........................... 81/9.43 |
| 2003/0069589 A1 * | 4/2003 | Small ............................. 606/120 |
| 2003/0110898 A1 * | 6/2003 | Tapper ........................... 81/9.43 |
| 2006/0271074 A1 * | 11/2006 | Ewers et al. ................... 606/148 |

\* cited by examiner

SURGICAL INSTRUMENT

FIELD OF THE INVENTION

The present invention relates to a surgical instrument and more particular to a surgical instrument for episiotomy and a method for episiotomy.

BACKGROUND ART

WO 00/57798 discloses an surgical cutting instrument comprising two legs, wherein one of said legs is provided with a cutting blade that is moved towards the other leg by exerting a downward force and by which a cutting procedure can be performed, commencing from the edge of the tissue portion for the removal of tensions, for example, during child-delivery. To this end, the instrument is embodied in such a manner that it is much easier to manipulate than scissoring instruments known in the prior art.

Practice has shown that in many applications, such as when an episiotomy is performed wherein tissue is subjected to tension, after making an initial incision of the edge, separation of the tissue into two parts is performed in an uncontrolled manner. This has the drawback that the tension cannot be extenuated in the desired manner, which makes the later healing process considerably more difficult. Above all, the improper separation of the tissue makes the joining thereof by suture considerably more difficult.

A sealing device is known from EP 1645238 A1 that operates like a pair of scissors and is provided with clamping jaws which can be used to engage and seal an artery or other portion of tissue. A cutting blade can be inserted into one of the clamping jaws with some sort of construction. If, for example, an artery is sealed, this can then be separated after the sealing procedure with a separate lever mechanism.

FR 1024981 discloses scissors wherein one of the scissor blades has been curved such that cutting is effected from the extremity of the blade of the scissors.

SUMMARY OF THE INVENTION

It is an object of the present invention to provide a surgical instrument that is easily manufactured, that is preferably disposable and which can be used, in particular, to perform an episiotomy.

More particular it is an object of the present invention to effect episiotomy under safe conditions such that it is fully guaranteed that the head of the baby to be born is never endangered.

It is a further object of the present invention to provide an instrument which can be manipulated with high accuracy in order to provide precise positioning and cutting.

In accordance with the invention a surgical instrument is provided for the removal of tension in a continuous portion of tissue, comprising, when in use, a U-shaped member with two opposing legs, wherein the space between said legs of said U member is embodied to receive a portion of tissue, wherein one of the legs of said U-shaped member is provided with an operative tissue-perforating member within said space between said legs, and the other of said legs is provided with a tissue supporting member, wherein the perforating member can be moved towards said supporting member, wherein said legs can be actuated to move towards each other, wherein one of said legs on the side facing away from the space between said legs is provided with a comb for defining a finger accommodation on both sides thereof.

Moreover the invention provides a method for episiotomy through the removal of the tension in a continuous portion of tissue by separating a portion thereof from the edge of said tissue portion to a certain point thereof, wherein said separation comprises a clear-cut separation by applying pressure from one side of said tissue portion and by supporting the other side thereof, wherein said separation comprises an initial separation procedure and a subsequent further separation procedure, wherein said initial separation procedure comprises separation at said particular point.

The mechanism for operation of the two legs acting relative to each other can include any cooperating set of cutting implements. For example it is possible that legs are pivotally connected to each other and that one of the legs is provided with a knife-like structure whereas the other is received with an anvil-like counterpart which can be effected as accommodation to fully receive the knife portion. The knife portion can either be fixed to the related leg or can be operated through a mechanism separate from such leg. The knife can comprise a straight blade or curved blade but can also include (part of) a wheel or tipped member which can make a sliding movement along the anvil part.

According to a preferred embodiment of the present invention a separate operating mechanism for the perforating member, such as a cutting blade, can be no longer present. One of the legs is coupled directly to the perforating member, whereas the other leg is provided with the contra-acting member that acts cooperatively with the perforating member. Moreover, according to a preferred embodiment of the present invention, as opposed to constructions known in the prior art, the initial separation of the tissue is not performed close to the edge of the tissue but at a point located more within the tissue. Perforation at that point will hardly reduce the tension in the tissue, or not at all. This is because, in general, the greatest degree of tension will be present at the free outer edge of the tissue. By creating the separation of the tissue in the direction of the edge after making a perforation, this separation can be performed in a controllable manner. In other words, as opposed to the prior art, there is not the risk of the uncontrollable parting of the tissue into tissue portions when this is commenced from the edge. This is because the separation takes place from a position located at a distance from the edge and from that position in the direction of the edge.

The creation of the first incision in the tissue can be performed in various ways. An example is mentioned here of the use of a separating blade, wherein the position of the blade in respect of the tissue to be separated is such, that when the blade is moved towards the corresponding support surface, the tip of the blade near the free end initially comes into contact with the tissue, after which separation in the direction of the edge of the tissue occurs. This can be achieved, for example, in that the receiving means for the blade is embodied at an angle in an upwardly inclined direction. Another option is to embody the cutting edge not as a curved blade and in such a manner that the initial contact can be achieved at the desired point.

Yet another option for making the perforation is, notably, with the use of a perforator, wherein the initial separation is performed at a distance from the edge of the tissue. Further separation towards the edge, for example, can be performed with the use of a perforator or a cutting blade but can also be (partially) initiated by making that initial perforation with a perforator. Other options for separating tissue are the use of a thin cutting wire, a scalpel that can be moved in the one leg and laser and water-jet techniques.

The relative movement of the legs of the U-shaped member can be implemented in any way. A parallel displacement with the use of the corresponding construction is possible. According to one advantageous embodiment of the invention, the legs are hingeably attached.

If a perforator or cutting blade is used for the separation of the tissue, for full perforation of the tissue in the opposing part of the other leg. An accommodation is preferably present in the other leg for receiving the respective perforating member.

It is possible embody the above-described instrument as a pair of scissors, i.e. that the legs in the accommodation hinged alternative embodiment of the invention are extended beyond the hinge and that those extensions are provided with finger holes for inserting the fingers of the physician or midwife. However, it is also possible for the legs themselves to be provided with receiving means for receiving the fingers (and thumb) of the user. In other words, the respective legs can be provided with engaging means for engaging the hand. More specifically, the construction is embodied in such a manner that the one leg is provided with a receiving means for receiving the fingers of the user and the other leg is provided with a receiving means for receiving the thumb of the user. More specifically, the other leg is provided with a means for receiving two fingers, wherein the separation of the fingers occurs by means of a comb mechanism inserted therein. This can also be embodied concavely so that, as described above, it may also serve as an accommodation for receiving the perforating member. In doing so, the accommodation is preferably somewhat rotated in respect of the separation plane between the two fingers so that it is adapted optimally to the natural position of the hand. More specifically, the thumb is supported in the longitudinal direction thereof, i.e. the respective accommodation also extends concavely in the longitudinal direction from the hinging point of both legs. In this manner, and especially in conjunction with the use of the above described comb, a very stable engagement of the instrument can be achieved, thus enabling optimum manipulations in complex positions, whilst full control of the instruments is retained and so the perforating procedure can be performed in a controlled manner.

According to the present invention, it is possible for the hinge between both legs to be embodied as a separate hinge. More specifically, preference is given to said hinge being embodied as a film hinge. Moreover, it is possible to embody the perforating member as a blade in plastic. Consequently, it is possible for the surgical instrument according to the present invention to be manufactured as a single part from a synthetic material by way of injection moulding. In this manner, a cheap disposable instrument can be obtained.

The invention also relates to a method for the removal of the tension in a continuous portion of tissue by separating a portion thereof from the edge of said tissue portion to a certain point thereof, wherein said separation comprises a clear-cut separation by applying pressure from one side of said tissue portion and by supporting the other side thereof, wherein said separation comprises an initial separation procedure and a successive further separation procedure, wherein said initial separation procedure comprises separation at that particular point.

DESCRIPTION OF THE DRAWINGS

The invention will now be described in more detail below with reference to exemplary embodiments shown in the drawing, in which.

DESCRIPTION OF THE PREFERRED EMBODIMENTS

Figure 1:
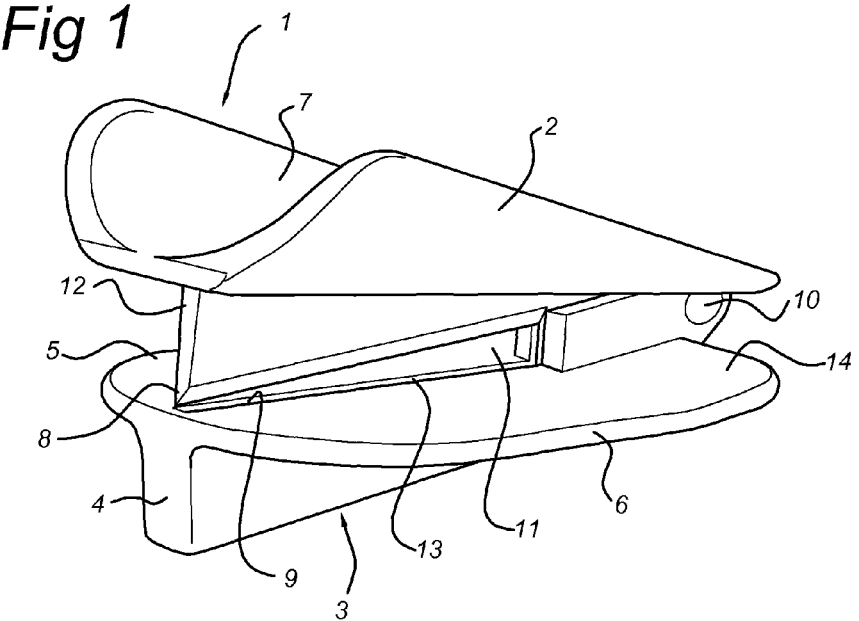
FIG. 1 shows a first embodiment of the invention in perspective.

In FIG. 1 the surgical instrument according to the present invention is indicated by the numeral 1. This comprises two hingeably connected legs, the one leg 2 and the other leg 3, wherein the hinge is indicated by the numeral 10. A space 11 is defined between the legs of the U-shaped member. A spring mechanism or the like can be present in order to force the legs 2 and 3 apart when not in an activated position.

The one leg 2 is provided on its upper side (as seen in the drawing) with a finger receiving means 7 and more specifically a receiving means for receiving the thumb.

The other leg 3 is provided with supporting surface 5, 6 for two fingers and positionability of the device using the two fingers can be achieved by a comb 4 which is clampingly engaged between the related fingers.

The upper side of the other leg is a plateau, indicated by the numeral 14. This plateau 14 is arranged at an angle and a groove 13 is provided therein for receiving a cutting blade 8 that is attached to the one leg 12. As will be apparent from the drawings, this blade has a particular shape. This is embodied straight and in such a manner that the part of the blade near to the free end 12 is located at a relatively small distance from the plateau 14 since the flat surface, as described above, is embodied at an angle.

Figure 2:
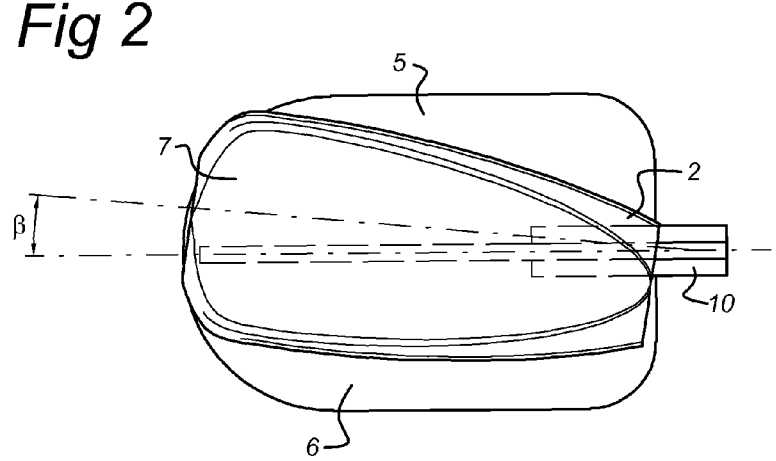
FIG. 2 shows a top view of a construction according to FIG. 1.
Figure 3:
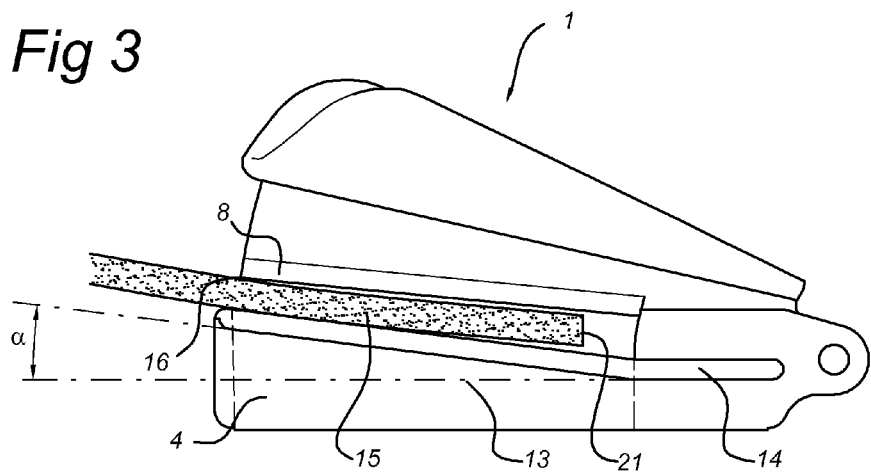
FIG. 3 shows the first step of performing the incision according to FIG. 1 and FIG. 2.
Figure 4:
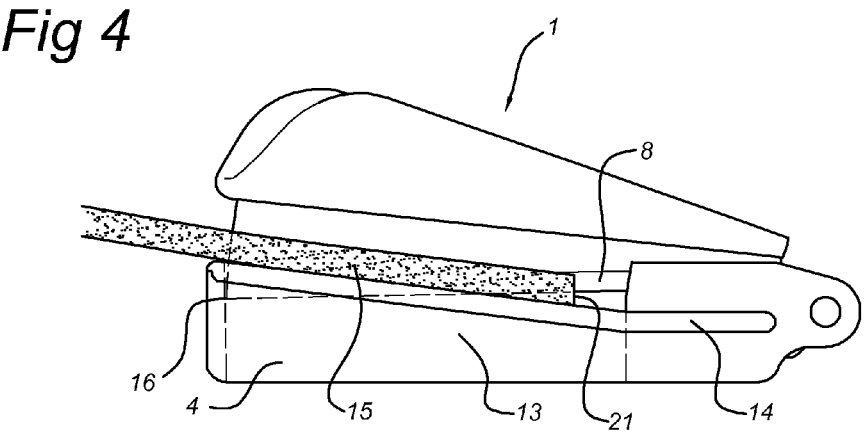
FIG. 4 shows a following step of performing the incision using the device according to FIG. 1 and FIG. 2.
Figure 5:
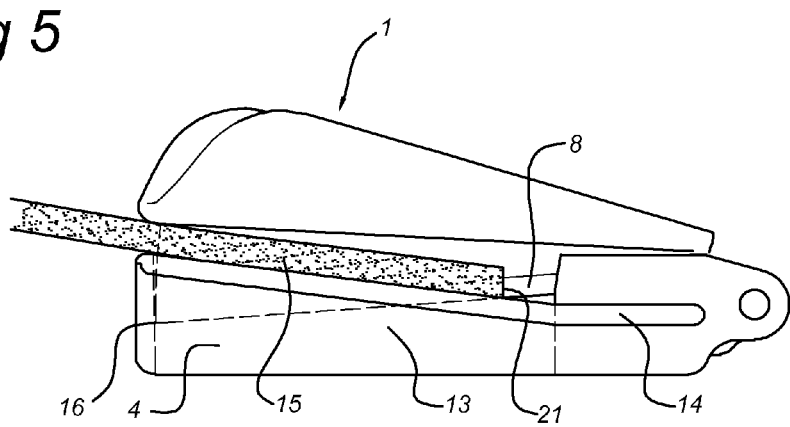
FIG. 5 shows the step of performing the full separation of the tissue.

The effect of this measure is illustrated in FIGS. 3-5. In FIG. 2, the surgical instrument 1 according to the invention is drawn in its opened position as the tissue 15 under tension is inserted with a free end edge 21. When the legs 2 and 3 are moved towards each other, the situation arises, as is shown in FIG. 3, wherein the portion of the blade 8 located nearest to the free end of the one leg 2 initially perforates the tissue 15 at point 16. At that moment, the remaining portion of the tissue 15, i.e. the portion of the tissue 15 lying between point 16 and the free edge 21, is still fully intact. The further movement of the legs 2 and 3 results in the situation shown in FIG. 4. This means that, commencing from the position shown in FIG. 3, more specifically point 16, the tissue is separated from point 16 in the direction of the free edge 21.

This results in the gradual and assured reduction of the tensions prevailing at the free edge 21. This as opposed to the constructions according to the prior art, wherein the initial separation takes place near to the edge 21 and then progresses in the direction of point 16.

FIG. 2 shows that the thumb accommodation is arranged at an angle in relation to the blade. This angle is indicated by 13 and preferably lies between 5-15° and is more specifically approximately 9°. This is most proximate to the natural position of the thumb in relation to the middle finger and forefinger when a squeezing action is performed.

Figure 6:
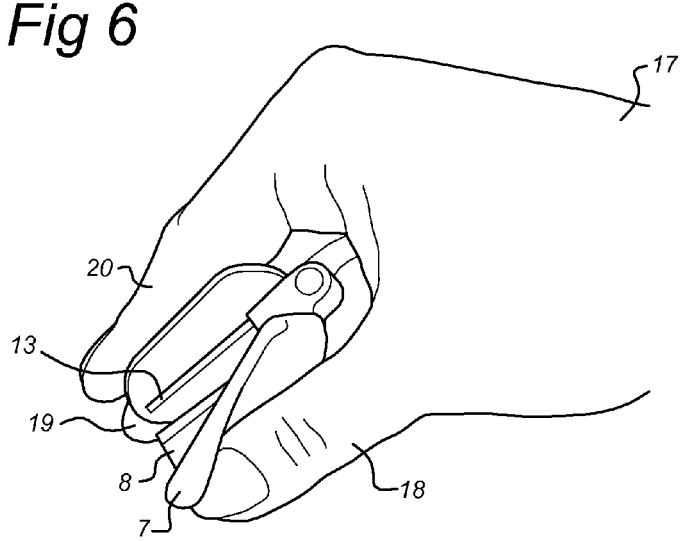
FIG. 6 shows the method for holding the device according to FIGS. 1-5.

FIG. 6 indicates how the surgical instrument 1 according to the invention is operated. The hand of the person performing the medical procedure is indicated by the numeral 17, the thumb by 18, the forefinger by 20 and the middle-finger by numeral 19. The device can be used both by left-handed and right-handed persons. The device can be embodied both as a disposable (entirely from a plastic material and/or in conjunction with steel for the blade) and as a re-usable, in which case it is preferably manufactured from a stainless steel material or other material that can be easily sterilized. An example of another such material is a glass-fibre reinforced plastic material such as polyamide with a sufficient glass-fibre content or other hard material in order to enable sterilization.

Figure 7A:
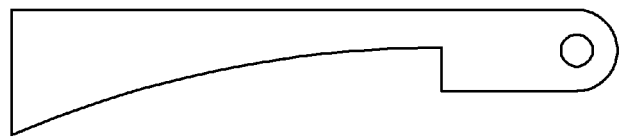
FIG. 7 shows alternative embodiments of the cutting blade.
Figure 7B:
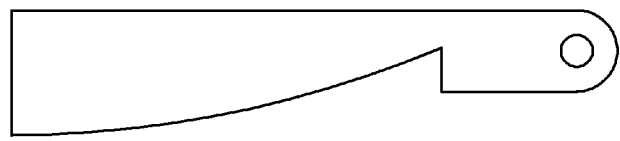
Figure 7C:
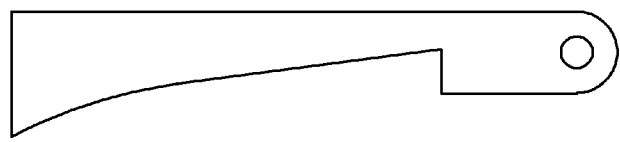

FIG. 7 shows a number of alternative embodiments. Here, the plateau 14 cannot be embodied at an angle and/or be inclined differently.

Figure 8:
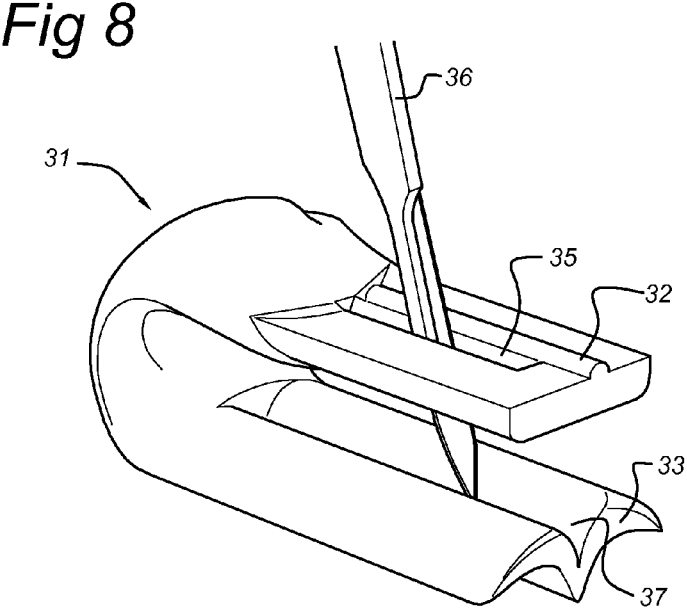
FIG. 8 shows a first alternative embodiment of the invention.
Figure 9:
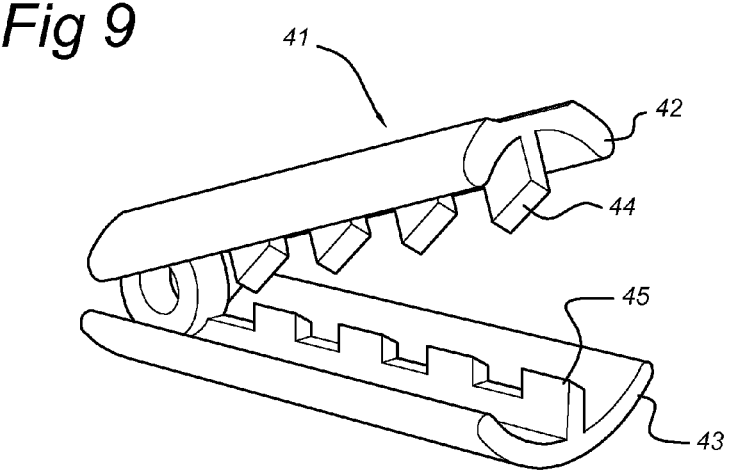
FIG. 9 shows a second alternative embodiment of the invention.

FIGS. 8 and 9 show alternative embodiments of the present invention. The alternative embodiment of FIG. 6 is indicated in its entirety by the numeral 31. The one leg 32 in this alternative embodiment is attached in a fixed position to the other leg 33. The one leg 32 is provided with a slit 35 for the movable insertion of a scalpel 36. The other leg 33 is provided with a receiving means 37 for the scalpel 36.

The alternative embodiment of FIG. 9 is indicated in its entirety by the numeral 41. The one leg 42 is hingeably attached to the other leg 43. A number of cooperative protruding perforating elements 44, 45 are present so that a perforation can be made in the respective tissue commencing from the previously indicated point 16 of the tissue 15 in the direction of the wall 21. It is presumed that, on perforation, the tissue will automatically part between the portions of tissue and that perforation will also promote the healing process.

After reading the foregoing, those skilled in the art will become readily aware of alternative embodiments. As already described in the foregoing, it is possible to extend the respective legs and to provide them with grips for the finger so that at scissor-like construction is obtained. Other forms of (parallel) articulation are also conceivable.

The invention claimed is:

1. A surgical instrument for the removal of tension in a continuous portion of tissue, comprising:
   (a) a U-shaped member with a first leg and a second opposing leg hingeably attached at a hinged end,
   (b) the first leg comprising a tissue supporting member embodied to receive a portion of tissue positioned on the side facing the space between the legs and a comb for defining a finger accommodation on both sides thereof provided on the side facing away from the space between said legs;
   (c) the second leg comprising a tissue perforating member positioned on the side facing the space between said legs, wherein the perforating member:
      (i) extends longitudinally along a length of said leg from the hinged end to a free end opposite the hinged end, and
      (ii) extends at an angle relative to the tissue supporting member such that a space is defined between the perforating member and the tissue supporting member near the hinged end of the instrument when a portion of the perforating member nearest the free end is moved towards the tissue supporting member and fully perforates the continuous portion of tissue at a point nearest the free end.

2. The surgical instrument according to claim 1, wherein said perforating member is immovably attached to the second leg.

3. The surgical instrument according to claim 1, wherein said perforating member extends substantially the entire length of said second leg.

4. The surgical instrument according to claim 1, wherein said tissue supporting member is provided with an accommodation for receiving said perforating member.

5. The surgical instrument according to claim 4, wherein said accommodation is provided in said comb.

6. The surgical instrument according to claim 1, wherein the second leg is provided with engaging means to be engaging by an accommodation hand on the side facing away from the perforating member.

7. The surgical instrument according to claim 6, wherein the second leg is provided with a means for receiving a thumb for support of the thumb in a longitudinal direction and the first leg is provided with the comb having a centre-line at an angle of 5-15°.

8. A method for episiotomy comprising:
   (a) supporting a continuous portion of tissue under tension on a one side of a tissue supporting member;
   (b) perforating said continuous tissue portion at a point within said continuous tissue portion that is not close to an edge of said continuous tissue portion, wherein said perforating said continuous tissue portion does not perforate the edge of said continuous tissue portion; and
   (c) subsequently separating said continuous tissue portion from the point within said continuous tissue portion to the edge of said continuous tissue portion.

9. The method according to claim 8, wherein said perforating step does not substantially reduce the tension in said tissue portion.

10. A surgical instrument comprising:
    a first leg with a free end and a perforating member positioned near the free end of the first leg and extending longitudinally along a length of the first leg;
    a second leg with a free end and a tissue supporting member, the second leg connected to the first leg on an end opposite from the free ends to form a U-shape; and
    a comb on one of the first and second legs for defining a finger accommodation on both sides thereof;
    wherein the legs can be actuated to move towards each other,
    wherein the perforating member is at an angle relative to the tissue supporting member such that a space is defined between the perforating member and the tissue supporting member near the end opposite from the free ends when a portion of the perforating member nearest the free end is moved towards the tissue supporting member and fully perforates the continuous portion of tissue at a point nearest the free end.

11. The surgical instrument of claim 10, wherein the perforating member is mounted in such a way that perforation commences from the free end of the legs when the legs are moved towards each other.

12. The surgical instrument of claim 10, wherein the perforating member is shaped so that perforation commences from the free end of the legs when the legs are moved towards each other.

13. The surgical instrument of claim 10, wherein the second leg further comprises an accommodation for receiving the perforating member.

14. The surgical instrument of claim 10, wherein the first leg is hingeably connected to the second leg.

15. The surgical instrument of claim 1, wherein the perforating member comprises a single blade.

16. The surgical instrument of claim 1, wherein the perforating member comprises a cutting blade.

17. The surgical instrument of claim 16, wherein the cutting blade is a straight blade.

18. The surgical instrument of claim 16, wherein the cutting blade is a curved blade.

\* \* \* \* \*